United States Patent
Rueckert et al.

(10) Patent No.: US 9,869,674 B2
(45) Date of Patent: Jan. 16, 2018

(54) METHOD FOR DETERMINING THE PRESENCE OF AN ANALYTE BY MEANS OF SMALL MAGNETIC PARTICLES, AND CORRESPONDING DEVICE

(75) Inventors: Martin Rueckert, Wuerzburg (DE); Volker C. Behr, Gerbrunn (DE); Thomas Kampf, Wuerzburg (DE)

(73) Assignees: Hochschule für angewandte Wissenschaften Fachhochschule Würzburg-Schweinfurt, Würzburg (DE); Julius-Maximilians-Universität-Würzburg, Würzburg (DE)

( * ) Notice: Subject to any disclaimer, the term of this patent is extended or adjusted under 35 U.S.C. 154(b) by 531 days.

(21) Appl. No.: 13/638,637

(22) PCT Filed: Apr. 1, 2011

(86) PCT No.: PCT/EP2011/001650
§ 371 (c)(1),
(2), (4) Date: Dec. 11, 2012

(87) PCT Pub. No.: WO2011/120712
PCT Pub. Date: Oct. 6, 2011

(65) Prior Publication Data
US 2013/0157256 A1 Jun. 20, 2013

(30) Foreign Application Priority Data
Apr. 1, 2010 (DE) .................. 10 2010 013 900

(51) Int. Cl.
*G01N 33/569* (2006.01)
*A61B 5/05* (2006.01)
(Continued)

(52) U.S. Cl.
CPC ......... *G01N 33/569* (2013.01); *A61B 5/0035* (2013.01); *A61B 5/055* (2013.01);
(Continued)

(58) Field of Classification Search
CPC .......... G01N 33/54326; G01N 33/569; G01N 33/5695; G01N 33/56983; G01N 33/6854; C12Q 1/04
(Continued)

(56) References Cited

U.S. PATENT DOCUMENTS 5,486,457 A * 1/1996 Butler .................. C12M 35/06
436/526
7,619,408 B2 11/2009 Gleich et al.
(Continued)

FOREIGN PATENT DOCUMENTS

WO    WO2004091386 A2    10/2004
WO    WO2004091390 A2    10/2004
(Continued)

OTHER PUBLICATIONS

Weizenecker, J., et al., "Three-Dimensional Real-Time In Vivo Magnetic Particle Imaging," Physics in Medicine and Biology; 2009, vol. 54, pp. L1-L10.
(Continued)

*Primary Examiner* — Melanie Yu Brown
(74) *Attorney, Agent, or Firm* — Mendelsohn Dunleavy, P.C.; Steve Mendelsohn (57) ABSTRACT

The invention relates to a method for determining the presence of an analyte by means of a distribution of small magnetic particles. According to said method, the magnetizations of the small particles are oriented in relation to each other by means of an outer magnetic focusing field; once the focussing field has been terminated, the magnetizations of the small particles are rotated asynchronously to the mag-
(Continued)

netic field by means of an outer magnetic field of suitable field intensity and rotational frequency, which rotates about a longitudinal axis (z); the temporal course of the superpositioned transverse magnetization of the set of particles is detected; and the presence of the analyte is deduced from the detected temporal course. The invention also relates to a corresponding device (1).

13 Claims, 5 Drawing Sheets (51) Int. Cl.
A61B 5/055 (2006.01)
G01N 33/543 (2006.01)
G01R 33/12 (2006.01)
A61B 5/00 (2006.01)
C12Q 1/04 (2006.01)
G01N 33/68 (2006.01)

(52) U.S. Cl.
CPC ........... A61B 5/0515 (2013.01); C12Q 1/04 (2013.01); G01N 33/54326 (2013.01); G01N 33/5695 (2013.01); G01N 33/56983 (2013.01); G01N 33/6854 (2013.01); G01R 33/1269 (2013.01)

(58) Field of Classification Search
USPC ........................................................ 436/526
See application file for complete search history.

(56) References Cited

U.S. PATENT DOCUMENTS

| 7,747,304 | B2 | 6/2010 | Gleich |
| 7,994,786 | B2 | 8/2011 | Weaver et al. |
| 8,305,076 | B2 | 11/2012 | Sack et al. |
| 8,532,735 | B2 | 9/2013 | Gleich |
| 2004/0033627 | A1 | 2/2004 | Aytur et al. |
| 2006/0189868 | A1* | 8/2006 | Gleich ............... A61B 5/0048 600/437 |
| 2006/0205093 | A1* | 9/2006 | Prins ............... G01N 33/54333 436/526 |
| 2006/0211938 | A1 | 9/2006 | Gleich et al. |
| 2006/0211941 | A1 | 9/2006 | Gleich |
| 2006/0248944 | A1 | 11/2006 | Gleich et al. |
| 2008/0220411 | A1* | 9/2008 | McNaughton ... G01N 33/54313 435/5 |
| 2008/0309330 | A1 | 12/2008 | Ohyu et al. |
| 2009/0227044 | A1* | 9/2009 | Dosev ............... G01N 33/54333 436/526 |
| 2010/0066363 | A1 | 3/2010 | Brazdeikis et al. |
| 2010/0179412 | A1 | 7/2010 | Weizenecker et al. |

FOREIGN PATENT DOCUMENTS

| WO | WO2004091408 A2 | 10/2004 |
| WO | WO2008099331 A1 | 8/2008 |
| WO | WO2009008956 A2 | 1/2009 |
| WO | WO2009037636 A1 | 3/2009 |
| WO | WO2010041178 A1 | 4/2010 |

OTHER PUBLICATIONS

Biederer, S., et al., "A Spectrometer for Magnetic Particle Imaging," IFMBE Proceeding 2008, vol. 22, pp. 2313-2316.
Weizenecker, J., et al., "A Simulation Study on the Resolution and Sensitivity of Magnetic Particle Imaging," Physics Medicine and Biology; 2007, vol. 52, pp. 6363-6374.
English Translation of the International Preliminary Report on Patentability and Written Opinion; dated Oct. 11, 2012 for corresponding PCT/EP2011/001650.
International Search Report and Written Opinion; dated Aug. 29, 2011 for corresponding PCT/EP2011/001650.
Carr, H. Y., et al.; "Effects of Diffusion on Free Precession in Nuclear Magnetic Resonance Experiments"; Physical Review, vol. 94, No. 3; May 1, 1954; pp. 630-638; XP5004628.

* cited by examiner

Fig. 1

$$MFI = [5a, 5b]$$
$$MFII = [5a, 5b; 6a, 6b]$$
$$MFIII = [P1 - P4]$$

METHOD FOR DETERMINING THE PRESENCE OF AN ANALYTE BY MEANS OF SMALL MAGNETIC PARTICLES, AND CORRESPONDING DEVICE

The invention relates to a new method for determining the presence of an analyte using a distribution of small magnetic particles. Furthermore, the invention relates to an apparatus that is suitable to carry out this method.

A method of the type mentioned in the introduction is known from US 2008/0220411 A1. Here, asynchronous rotation of the magnetization of a correspondingly prepared small magnetic particle in a rotating external magnetic field is used to determine the presence of an analyte, for example of a bacterium, a virus, a biological cell, a protein or a nucleic acid. The disclosed method is based on the fact that the rotation of the small magnetic particles or their magnetization in an external rotating magnetic field decays in dependence on field strength and rotation frequency, into a region of synchronous rotation and into a region of asynchronous rotation.

In the case of a mechanically rotating small particle, this behavior is due to friction terms with respect to the environment. If the magnetization rotates in the crystal lattice of the small particle, other, internal friction terms are responsible. If the torque transferred from the external magnetic field is too low with respect to the friction terms, the magnetization or the small particle drags relative to the rotation of the magnetic field because it wishes to tarry with respect to the environment. The result is a non-linear fluctuation in the rotation of the magnetization relative to the rotation of the magnetic field. On average, a measurable rotation drift results.

According to US 2008/0220411 A1, the magnetization of a small particle rotates in dependence on the field strength of the external magnetic field synchronously with the rotation of the magnetic field on average up to a critical frequency $\Omega_c$. If the rotation frequency of the magnetic field exceeds the critical rotation frequency $\Omega_c$, the magnetization of the small particle rotates asynchronously at a reduced average rotation frequency. This average, asynchronous rotation of the magnetization can be observed as a frequency term of the magnetization. A lower critical average rotation frequency $\Omega_c$ occurs at a smaller field strength than at a higher field strength. The relationship between critical average rotation frequency $\Omega_c$ and field strength B of the external magnetic field is given by:

$$\Omega_c = \frac{mB}{\gamma}.$$

Here, m is the magnetic moment of the small particle. The term $\gamma$ describes a friction term which, in the case of a mechanical rotation of the small particle, includes the viscosity of the environment and a shape factor of the small particle. In the case of a rotation of the magnetization in the crystal lattice of the small particle, the friction term $\gamma$ is to be ascertained empirically.

US 2008/0220411 A1 takes account of the fact that the non-linear rotation drift in the case of asynchronous rotation of the small particle changes in dependence on their binding or coupling state. If a small magnetic particle is prepared, for example, on its surface such that it binds to an analyte of interest, it is possible to draw conclusions relating to the presence of the analyte if a change in the non-linear rotation drift is observed. The coupled small particle has a reduced asynchronous rotation frequency with respect to the free small particle for example owing to its size increase. US 2008/0220411 A1 furthermore teaches the optical measurement of the rotation frequency of the small particles by observing them directly. For example, to this end, merely a hemisphere of the small particles is appropriately coated such that the rotation frequency can be observed directly from the change of the two hemispheres.

Disadvantageously, the method according to the prior art is limited to observing a macroscopic rotation of the bound small magnetic particle. Optical measurement is complex and prone to errors.

It is an object of the invention to specify a method for ascertaining the presence of an analyte using small magnetic particles, with which additional uses with respect to the prior art can be developed. It is a further object of the invention to specify an apparatus suitable for carrying out this method.

The object with respect to the method is achieved, according to the invention, in that firstly, the magnetizations of the small particles are aligned with one another using an external magnetic focusing field, after the focusing field has been switched off, the magnetizations of the small particles are set into a rotation which is asynchronous with the magnetic field using an external magnetic field of suitable field strength and rotation frequency that rotates about a longitudinal axis, subsequently the temporal profile of the superposed transverse magnetization of the particle ensemble is detected, and conclusions relating to the presence of the analyte are drawn from the detected temporal profile of the transverse magnetization.

Here, in a first step, the invention proceeds from the assumption of no longer detecting the asynchronous rotation of the small particles by optical means but using the superposed transverse magnetization of the particle ensemble. In an external rotating magnetic field, the magnetizations of the small particles are macroscopically aligned and rotate about the rotational axis of the magnetic field. The superposed transverse magnetization rotates in a projection into a plane perpendicular to the rotational axis. If the magnetizations of the small particles rotate in phase, the result is a maximum superposed transverse magnetization that rotates at the rotation frequency of the small particles. If the magnetizations of the small particles go out of phase, the observed transverse magnetization disappears with a characteristic decay period. If the magnetizations of the small particles are randomly aligned, the superposed transverse magnetization is no longer observable. On average, all magnetizations of the small particles then cancel each other out.

If the rotating external magnetic field is chosen such that the magnetizations of the small particles rotate asynchronously, the measurement frequency, i.e. the rotation frequency of the superposed transverse magnetization, is separate from the excitation frequency, i.e. the rotation frequency of the external field. The excitation signal does not crosstalk to the measurement signal. The sensitivity of the measurement is thus significantly improved. No complicated methods for separating the excitation signal from the measurement signal are necessary. A simple band-pass filter or low pass filter suffices for effective separation.

In a second step, the invention proceeds from the finding that a defined initial state of the observed system needs to be established in order to observe the superposed transverse magnetization. This initial state must differ at least from a state of the system in which the magnetic moments of the small particles have a random distribution. Accordingly, a defined disturbance must be introduced into the system such that the magnetizations of the small particles add up at least to an observable superposed transverse magnetization. To this end, an external magnetic focusing field is produced in a preparation step at the beginning of each measurement, as a result of which at least part of the magnetizations of the small particles are aligned with respect to one another. If a rotating external magnetic field with the appropriate strength and frequency is switched on after the focusing field has been switched off, the aligned magnetizations or magnetic moments of the small particles first rotate in phase starting from the defined start state, such that a superposed transverse magnetization can be observed.

In the simplest case, the frequency components of the superposed transverse magnetization of the particle ensemble are detected. Said frequency components in particular correspond to the rotation frequencies of the magnetizations of the small particles. If the magnetizations of the small particles all rotate in phase, the rotation frequency of the superposed transverse magnetization corresponds to the average rotation frequency of the magnetizations of the small particles. Owing to field inhomogeneities, dispersion of the particle characteristics and differences in the particular chemical environment, the magnetizations of the small particles exhibit a different asynchronous rotation drift, which results in increased dephasing. Different frequency components are detectable in the superposed transverse magnetization.

By analyzing the frequency components of the transverse magnetization, it becomes possible to draw conclusions relating to the presence of an analyte. If, for example, a prepared small particle couples as a probe to the analyte, or if the analyte binds to the surface of the small particle via receptors, with the size and shape of the bound small particle its asynchronous rotation drift changes as well. Using an analysis of the frequency components of the superposed transverse magnetization it becomes possible to draw conclusions relating to the presence of the analyte.

Furthermore, it is possible using the analysis of the frequency components of the transverse magnetization to draw conclusions relating to the physical and/or chemical environmental parameters of the analyte. In particular, for example, changes in the pH, the temperature or the viscosity of the environment of the analyte lead to changes in the frequency components of the detected signal.

On the other hand it is also possible to observe the change in magnitude of the transverse magnetization as a temporal profile of the transverse magnetization. This is because the transverse magnetization, which is at a maximum initially when the magnetizations of the small particles are rotating in phase, decays not only owing to the described field inhomogeneities and the existing dispersion of the particle characteristics, but in particular also owing to diffusion and friction terms. In what is referred to as Brownian relaxation, the small magnetic particles rotate mechanically. The relaxation is here dependent upon the size of the small particle and substantially on the viscosity of the surrounding medium. In the case of Néel relaxation, the magnetization of the small particles rotates in the crystal lattice. The relaxation is here dependent upon internal, empirically ascertained friction terms. If a small particle couples to an analyte, the observable relaxation time changes as a result. For small particles with particle diameters in the range of a few 100 nm, the rule of thumb is that free small particles show a faster relaxation of the superposed magnetization than bound or coupled small particles. By observing the decay behavior of the superposed transverse magnetization, it is to this extent possible again directly to draw conclusions relating to the presence of an analyte.

If, in the presence of the analyte, the small particles cluster together, this, too, can be observed via the decrease in the superposed transverse magnetization. This is because in this case the macroscopic magnetization, which is produced using the focusing field after the preparation of the sample, decays remarkably quickly when the external rotating magnetic field is applied because of the given mechanical and magnetic couplings of the individual particles in the cluster. This decay can be observed immediately when the rotating external magnetic field is switched on by way of a pulse-type profile of the superposed transverse magnetization.

By calibrating the recorded measurement curves of the transverse magnetization, it even becomes possible for further information relating to the analyte to be obtained. Examples of such information are the concentration or the type of the analyte.

The small magnetic particles used are ferromagnetic or superparamagnetic particles, which have as great a magnetic moment as possible relative to their volume. Such particles can for example be composed of iron oxide, but can also include for example cobalt, nickel or gadolinium. Suitable for use in biology and medicine are in particular magnetic nanoparticles with particle diameters between 20 and 200 nm. The greater the ratio between magnetic moment and volume, the greater the rotation drift relative to the external magnetic field in the case of asynchronous rotation.

The longitudinal axis or rotational axis, about which the external magnetic field rotates, does not necessarily have to be fixed in space for the purpose of the invention. Rather, the rotational axis of the magnetic field can also vary in terms of space, which is likewise included in the claimed subject matter.

In order to increase the compatibility of the small particles in medical engineering, the particle surface is provided with a coating. The coating can, for example, be composed of dextran molecules. For use of the small particles as probes, various functional groups are added to the particle surface. Said functional groups bind specifically to the analyte, such that the analysis can be matched especially to a particular analyte.

Acting as the target substance or analyte are for example receptors of macrophages, biomolecules or cells, also viruses, bacteria, molecules, macromolecules, antigens or antibodies. If the analyte binds to the functionalized surface of the small magnetic particles, the mechanical rotation in the external rotating magnetic field is relatively weakly damped. If the analyte to be observed has two or more bonds, aggregates are formed from the small particles, which results in a relatively strong impairment of the mechanical rotation. If the analyte also binds to small non-magnetic particles, the resulting aggregates change their hydrodynamic volume. The magnetic moment of the individual particle, however, persists. As a result, the impairment of the mechanical particle rotation is further increased.

If binding groups on cell walls or on objects that are considerably larger than the binding small particle is the aim of the analysis, the mechanical rotation in the asynchronous domain is effectively slowed or impaired. If appropriate, it is then possible to observe a rotation of the magnetization in the crystal lattice.

In a particularly advantageous embodiment, the described method is used to carry out a biopsy on a physiological or pathological tissue or an examination of blood or other body fluids taken. Used here are small magnetic particles with a prepared particle surface which bind to receptors of pathological cells or pathogens. In a target volume of only a few µl, it is possible to analyze in particular directly a biopsy needle with a diameter of less than 1 mm or a small liquid sample. The method allows for a quick and simple check as to whether the sample taken is pathological. In this way, diseases such as tuberculosis can be easily and quickly detected via the binding of the particles to the *Mycobacterium tuberculosis* in a sample of the expectoration of the patient.

In a preferred embodiment, the temporal profile of the transverse magnetization is detected only with a delay time after the focusing field is switched off. This takes into account the fact that in the case of the small particles that are relevant here, the macroscopic magnetization of an ensemble of aligned free small particles relaxes more quickly than the macroscopic magnetization of an ensemble of aligned bound small particles. If a delay time is introduced between the preparation of the sample and the reading external rotating magnetic field, the free small particles can be separated from the measurement signal. If the rotating external magnetic field is switched on after a delay time that is greater than the relaxation time of the magnetization of the free small particles, only the magnetizations of the bound small particles still contribute to the superposed transverse magnetization. The magnetizations of the free small particles at the time of the measurement are randomly distributed, such that their superposed transverse magnetization adds up to zero. The selectivity and the sensitivity of the measurement method are hereby improved.

The temporal profile of the transverse magnetization is expediently detected only after a dead time after the focusing field has been switched off. In this manner, the strong excitation signal of the focusing field is prevented by metrological means from being inductively included in the measurement signal. If the measurement of the superposed transverse magnetization is carried out in particular inductively, the measurement coil is ideally short-circuited or disconnected during the dead time, in order to suppress long post-pulse oscillation of the focusing pulse in the low pass.

In a more advantageous embodiment, the time derivation is formed from the profile of the transverse magnetization, and from the derivation conclusions relating to the presence of the analyte are drawn. As a result, changes in the transverse magnetization over time are more easily apparent. In particular, in the case of inductive measurement recording, a time derivation of the transverse magnetization results on account of the measurement method.

More advantageously, the direction of rotation of the rotating magnetic field is reversed with an echo frequency. Analogously to the spin echo from magnetic resonance imaging, it is possible by reversing the direction of the external rotating magnetic field to reverse the dephasing of the asynchronously rotating small particles. After the direction of rotation is reversed, at least part of the magnetizations of the small particles are once again in phase, as evidenced by an increase of the signal of the superposed transverse magnetization. The use of the echo method results, on account of the repeated signal recording, to an improved signal-to-noise ratio. In the time domain, a wider measurement signal is recorded, such that the bandwidth of the signal in the frequency space is reduced and thus metrologically optimized. It is furthermore possible to draw conclusions relating to the structure of the formed bound particles using observation of the decay rate of the echo signals. For example, anisotropic particles rotate out of the rotational plane of the magnetic field such that the dephasing caused thereby cannot be reversed even using echo methods.

The rotating magnetic field can be generated for example with a number of windings or coil arrangements, which can be supplied with current individually and are arranged in the circumferential direction. Here, the rotation field can be generated in particular in a single-phase or multi-phase manner. In a cost-effective variant which is simple in terms of construction, the rotating magnetic field is generated using two coil pairs, in particular Helmholtz coil pairs, which are mutually perpendicular. By way of alternatingly supplying the coil pairs with current, the rotating magnetic field is generated. The rotation frequency is controlled by timing the supply of current. The current flowing through the coils controls the strength of the rotating magnetic field.

In a further advantageous variant, the two coil pairs are driven using time-varying phase differences. This can be done using differing frequencies and/or differing phases. With such driving it is possible, from a temporal perspective, for the field of one coil pair to repeatedly overtake the other field such that the direction of rotation of the generated rotating magnetic field reverses as a result of a beat frequency of the two frequencies used. With such driving it is possible to relatively easily effect a periodically repeating reversal in the direction of rotation of the rotating magnetic field, such that the superposed transverse magnetization is recorded according to the echo method.

The focusing field can be produced by switching on a corresponding magnetic field generator. Since a sharp rectangular pulse in the frequency space generates an undesired amount of side bands (the higher-order harmonics), the focusing field is preferably switched on and off using a Gaussian pulse or using a sinc pulse or using a linear combination of Gaussian and/or sinc pulses. Since the frequency components of a Gaussian pulse are distributed only around the central frequency, it is possible for the excitation signal to be separated from the measurement signal by a low pass. A sinc pulse, that is to say a pulse of the function $\sin(t)/t$, constitutes the Fourier transform of a rectangular pulse. To this extent, a sinc pulse has a significantly more sharply delimited bandwidth in the frequency space than the Gaussian pulse. Continuous bandwidth-limited signals can be represented in particular as a linear combination of sinc pulses.

A directed focusing field results in an alignment of the magnetizations of the small particles and thus to an aligned macroscopic magnetization. To generate such a focusing field, preferably the magnetic field generator which is also used for generating the external rotating magnetic field can be used. For example, to this end, only one coil pair or one coil of the coil arrangements used is correspondingly driven.

In another variant, the focusing field is generated by the rotating magnetic field itself. Here, in particular the switching on of the rotating magnetic field suffices in order to attain a measurable disturbance of the randomly aligned magnetizations of the small particles. Advantageously, the focusing field is generated by increasing the field strength of the rotating magnetic field. By increasing the field strength, the magnetizations of the small particles are forced into a synchronous rotation with the external magnetic field. All magnetizations of the small particles then rotate in phase with the frequency of the rotation field. By subsequently lowering the field strength to the region of the asynchronous non-linear rotation, the prepared sample is then read. Although the provision of a focusing field is also possible by lowering the rotation frequency of the external rotating magnetic field, the distance between the excitation frequency and the measurement frequency is in this way reduced in a metrologically undesired manner.

In a further advantageous embodiment, the refocusing field is generated such that only the magnetizations of small particles of identical rotation characteristics are selectively set into a synchronous rotation. Here, use is made of the fact that the described critical frequency $\Omega_c$, which describes the transition between synchronous and asynchronous rotation, is also dependent on the volume or the shape of the small particles. This dependence results in the measurement signal of the detected superposed transverse magnetization to worsen with increasing bandwidth of the small particle variation. If, on the other hand, the refocusing pulse is generated such that only small particles of identical rotation characteristics are set into a synchronous rotation, only these contribute to the superposed transverse magnetization. The magnetizations of the other small particles are, however, randomly aligned. Overall, it is possible in this manner to obtain an improvement of the detected measurement signal without having to reduce the bandwidth of the sizes of the small particles used, which is likewise associated with high costs.

In particles with Néel relaxation, the size is effectively the decisive selection criterion. Generally, the ratio of magnetic moment of the particle and its friction term is decisive. In the case of massive particles with a magnetization that is fixed in the lattice, the friction term is independent of the size, and only depends on the shape factor. By suitably selecting the field strength and/or the rotation frequency of the refocusing field, particles of identical rotation characteristics, i.e. particles with the same rotation drift at the same field strength and the same rotation frequency, are thus selected.

Such selective refocusing can be achieved for example by a rotating magnetic field whose axis of rotation extends along a trajectory. In this case, there is refocusing only for very particular particles with an integer division ratio of their rotation frequency. This is because only those particles which have 1/n times the rotation frequency with respect to the rotation of the refocusing field (n: integer) go back into their initial position once the use of the 3D rotation field is complete. In this manner, it is possible to achieve highly selective refocusing pulses. The signal selection takes place using a suitable low pass or band pass filter.

By way of a comparison measurement with a defined sample, it becomes possible to draw conclusions relating to the concentration of the analyte on the basis of the detected temporal profile of the transverse magnetization. In principle, the magnitude of the transverse magnetization increases with the number of the coupled small particles in relation to their overall number.

In a preferred embodiment, the focusing field is generated between 10 ns and 10 ms with field strengths between 0.1 mT and 1 T in order to achieve alignment or rotation of the macroscopic magnetization or of the superposed transverse magnetization. Here, the longer pulse duration applies to the weaker field and the shorter pulse duration to the stronger field. Both variants have different requirements for the signal chain. For sample sizes of a few µl and switching-on times of a few µs, fields of 1 T are also relatively easily manageable. For an asynchronous non-linear rotation of the preferably used nanoparticles, the rotating magnetic field advantageously has field strengths between 0.1 mT and 100 mT and frequencies of 100 Hz to 100 MHz. The high frequencies are particularly suitable for small sample sizes because no physiological limit values must be observed.

In a more preferred embodiment, a space-dependent phase position is impressed on the particle ensemble using a gradient field switched on for a predetermined time interval. As long as the magnetic gradient field is switched on, the individual small magnetic particles rotate in a space dependent manner with in each case different asynchronous rotation frequencies, as a result of which a space-dependent phase position is produced after switching off. The gradient field is used before the actual measurement for spatial encoding via the establishing phase position. In an embodiment which is expedient for this, after the magnetic gradient field is switched off, a second identical magnetic gradient field with the opposite sign is produced with the same time interval. This method makes it possible to carry out a measurement of flow profiles or vessel structures.

Here, for a predetermined time duration, first a magnetic gradient is applied in a predetermined spatial direction in which the flow is meant to be measured. Subsequently, for the same time period, the same gradient with the same gradient strength but with the opposite sign is applied. Subsequently, the frequency distribution of the transverse magnetization is detected. The first two steps have the effect that unmoving small particles experience no phase change, because the second step quasi completely reverses the first step for resting particles. Particles moving in the direction of the gradient, however, experience a phase change which is proportional to the traveled distance. The phase change is thus a measure of the flow speed. It is possible in particular to derive the average flow rate. It is possible using this measure for example to monitor the flow rate of the investigated medium.

In order to be able to carry out flow measurement also with particles with great dispersion of rotation characteristics, a combination with a 180° spin flip is advantageous. After the refocusing pulse, an echo signal is produced, which occurs in the case of a resting particle at exactly twice the time between refocusing pulse and reversal of direction of rotation, as a result of the reversal of direction of rotation of the rotating magnetic field. The small particles, which meanwhile have gone out of phase owing to the particle characteristics, rotate in phase again after the reversal of direction of rotation, which results in an echo signal of the superposed transverse magnetization which has increased again in terms of intensity. When the small particle or the particle ensemble moves in the direction of the gradient, this echo signal is offset proportional to the speed, wherein any influence owing to the particle scattering is neutralized.

With respect to the apparatus, the object is achieved according to the invention by an apparatus for determining the presence of an analyte using small magnetic particles, which apparatus comprises a first magnetic field generator for generating a magnetic focusing field, a second magnetic field generator for generating a magnetic field which rotates about a longitudinal axis, a measurement device for detecting the temporal profile of the superposed transverse magnetization, and a control apparatus. The control apparatus is adapted for driving the magnetic field generators according to the abovementioned method and for outputting the temporal profile of the transverse magnetization or a variable derived herefrom for determining the presence of the analyte.

Preferably, the measurement device comprises a number of induction coils which are aligned with their axes of symmetry perpendicular to the longitudinal axis. The induction coils can be configured in particular as solenoid coils having a plurality of parallel windings. Via the induction coils, the temporal profile of the superposed transverse magnetization is directly detected as a measurement signal. The induction voltage here gives the temporal change of the transverse magnetization.

More preferably, the control apparatus is adapted for switching the first magnetic field generator on and off in the manner of pulses, and for switching on the second magnetic field generator only after a delay time after the first magnetic field generator has been switched off. Firstly, the delay time prevents crosstalk of the excitation signal to the measurement signal. Secondly, this delay time is used to separate free unbound small particles for the measurement signal on account of the shorter relaxation time of the superposed transverse magnetization.

If the control apparatus is adapted for switching on the measurement apparatus only after a dead time after the focusing field has been switched off, it is additionally prevented that on account of induction the excitation signal crosstalks to the measurement signal. To this end, preferably a switch element can be provided, which disconnects or short-circuits the measurement device during the dead time. If the receiver is not disconnected before a low pass, a rectangular impulse results in post-pulse oscillation of the low pass, as a result of which a long delay time results.

In a preferred alternative, the first and second magnetic field generators are combined into one generator. Here, this generator comprises more advantageously two pairs of coils which are arranged perpendicular with respect to each other, in particular Helmholtz coils. By separately driving a pair of the coils, it becomes possible to generate the directed focusing field. Alternatively it is also possible for the focusing field to be generated by switching on or by increasing the field strength of the rotating magnetic field. Here, the coil pairs are switched on or supplied with a correspondingly higher current.

To separate the rotation frequency of the rotating magnetic field from the frequency of the transverse magnetization, further preferably a low pass filter or a bandpass filter is provided.

In order to suppress induction voltages or currents, generated by the external magnetic field, in the measurement signal, the input signal of the second magnetic field generator is preferably coupled in anti-phase with the output signal of the measurement device, in particular with the coil output signal. This coupling can take place for example inductively using a transformer or the like.

Preferably, an active counter-coupling is also used to improve the measurement method. Here, the disturbance components in the receiving chain in a calibration measurement are detected. These disturbance components are then directly coupled into the receiving chain with the opposite sign in the actual measurement. To this end, advantageously a transformer or generally an RF transmitter is provided. The coupling-in signal is generated in particular using a digital-to-analog converter.

Exemplary embodiments of the invention are explained in further detail with reference to a drawing, in which.

Figure 1:
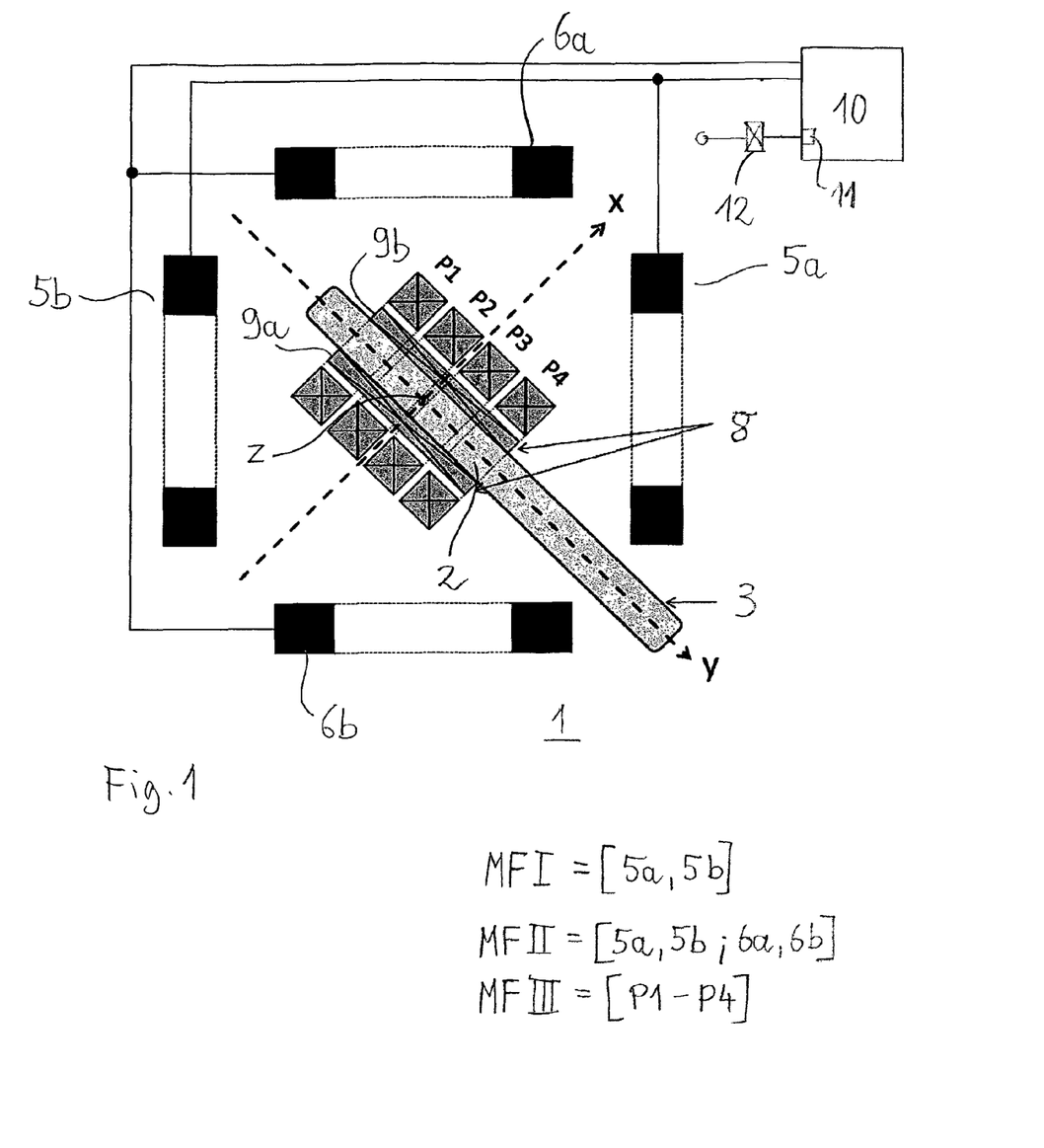
FIG. 1 schematically shows the construction of an apparatus for detecting an analyte using an ensemble of small magnetic particles.

FIG. 1 shows schematically an apparatus 1 for determining the presence of an analyte using an ensemble of small magnetic particles. In a measurement volume 2, here the superposed transverse magnetization of an ensemble of small magnetic particles in a sample 3 is observed. The sample 3 is here, for example, a biopsy needle with a tissue sample. The added small magnetic particles have a functionalized surface which couples to receptors of pathological cells.

To generate an external magnetic field rotating about the longitudinal axis z, a first Helmholtz coil pair 5a, 5b and a second Helmholtz coil pair 6a, 6b are provided. The two Helmholtz coil pairs 5a,b and 6a,b are here arranged orthogonally with respect to one another. The magnetic field rotating about the longitudinal axis z comes about owing to the alternating supply of current to the two Helmholtz coil pairs 5a,b and 6a,b.

Two induction coils 9a and 9b are arranged laterally next to the measurement volume 2 as a measurement device 8 for detecting the temporal profile of the superposed transverse magnetization. The axis of symmetry of the two induction coils 9a,b is perpendicular to the longitudinal axis z.

A control apparatus 10 is provided for controlling the Helmholtz coil pairs 5a,b and 6a,b and for reading the measurement device 8.

Furthermore, along the sample direction y, a number of coil pairs P1 to P4 are arranged. These coil pairs P1 to P4 can be used for generating a focusing field. In particular, it is possible, using separate driving of the four coil pairs P1 to P4 for a gradient field and in particular a gradient field migrating in the y direction to be produced. Such a gradient field and in particular such a migrating gradient field serves for a specific preparation of the sample, to be precise in particular impressing a space-dependent phase profile of the rotating magnetizations of the small particles, as is necessary for an imaging method. For purely detecting the presence of an analyte, the coil pairs P1 to P4 are not necessary.

For detecting an analyte, for example a pathological cell or the like, current is supplied in a pulsed manner using the control apparatus 10 initially to the Helmholtz coil pair 5a, 5b, such that a directed magnetic focusing field prevails at the measurement volume 2 for a short time interval. The focusing field is here directed in a direction parallel to the main axis of symmetry of the Helmholtz coil pair 5a, 5b. Supplying current to the Helmholtz coil pair 5a, 5b is here selected such that the field strength of the magnetic focusing field aligns the magnetizations of the small magnetic particles for a macroscopic magnetization. In order to suppress undesired frequency components in the measurement signal, the Helmholtz coil pair 5a, 5b is supplied with current such that a sinc-pulse-shaped magnetic field is produced as the focusing field.

After a delay time, the control apparatus 10 provides currents to both Helmholtz coil pairs 5a,b and 6a,b in alternation such that an external magnetic field rotating about the longitudinal axis z is generated in the measurement volume 2. The field strength and the rotation frequency of this magnetic field are selected such that the magnetizations of the small magnetic particles rotate asynchronously. The delay time between the application of the focusing field and the application of the rotating magnetic field is set such that the macroscopic magnetization of the free small particles on account of diffusion effects etc. is already decayed when the rotating magnetic field is switched on. Since the decay of the macroscopic magnetization of the bound small particles is slower, at least a residual amount of the magnetization of the bound small particles is still present at the time of the switching-on of the rotating magnetic field.

After the rotating magnetic field is switched on, the magnetizations of the bound small particles begin to rotate asynchronously such that using the two induction coils 9a,b the temporal profile of the superposed transverse magnetization in the x, y plane can be observed. If the specific analyte is not present in the sample, no signal is generated by the application of the reading rotating magnetic field. If the analyte is present, this results in the formation of bound small magnetic particles. When the readout field is switched on, a superposed transverse magnetization is detectable as a measurement value. Said superposed transverse magnetization is detected using the induction coils 9a,b as a time-varying measurement signal, because the superposed transverse magnetization rotates with a central asynchronous rotation frequency in the x,y plane. The presence of a measurement signal to this extent shows the presence of the analyte directly. In particular provided is a quick and meaningful method for determining for example whether a tissue taken is pathological.

The described measurement method with the apparatus 1 shown in FIG. 1 is characterized in that the Helmholtz coil pair 5a,b is used as a first magnetic field generator MFI. The Helmholtz coil pairs 5a,b and 6a,b are used as the reading magnetic field generator MFII. With appropriate provision of current, the desired rotating external magnetic field results. Alternatively to the Helmholtz coil pair 5a,b, it is possible to use the sequence of the coil pairs P1 to P4 as a first magnetic field generator MFIII. The number of coil pairs is here arbitrary.

In order to short-circuit or disconnect the measurement coils 9a,b, a corresponding switch element 11 which is actuatable by the control apparatus 10 is provided. The separation of the excitation signal from the measurement signal is carried out by a low pass filter 12.

Figure 2:
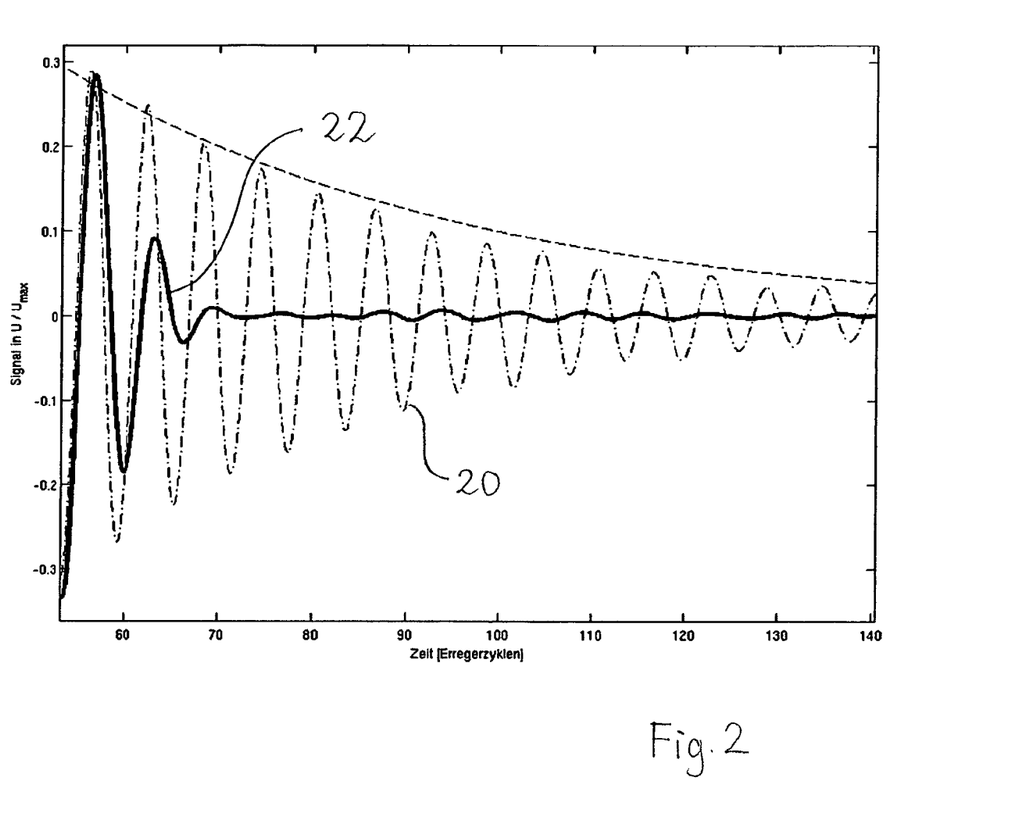
FIG. 2 shows the decay behavior of the superposed transverse magnetization for two exemplary cases.

FIG. 2 shows, for explanation reasons, the temporal profile of a superposed transverse magnetization 20 of a simulated first ensemble of small magnetic particles. In this simulation, diffusion effects, which result in a loss of coherence of the individual asynchronously rotating magnetizations of the small particles, are taken into account. After preparing the sample using a magnetic focusing field of suitable strength, when an external rotating magnetic field of corresponding field strength and rotation frequency is applied, the magnetizations of the small particles begin to rotate asynchronously. The central asynchronous rotation frequency observable via the superposed transverse magnetization can be seen in FIG. 2 directly from the profile of the transverse magnetization. On account of loss of coherence owing to the diffusion, with each post-pulse oscillation the amplitude of the observable superposed transverse magnetization decreases. The envelope plotted in dashed lines shows the relaxation time caused by diffusion effects.

In addition, the profile of the superposed transverse magnetization 22 of a simulated ensemble of small magnetic particles is shown, wherein the particles have a 20% variation in their characteristics. In addition, a 20% variation of the field strength inside the measurement volume is also associated with the rotating external magnetic field.

It becomes clear that the relaxation time of the second particle ensemble is considerably shorter than for the first particle ensemble. In addition to diffusion effects, the variation of the particle characteristics and the field inhomogeneities result in a much quicker dephasing of the individual magnetizations of the small particles and thus to a quicker decay of the superposed transverse magnetization.

Figure 3:
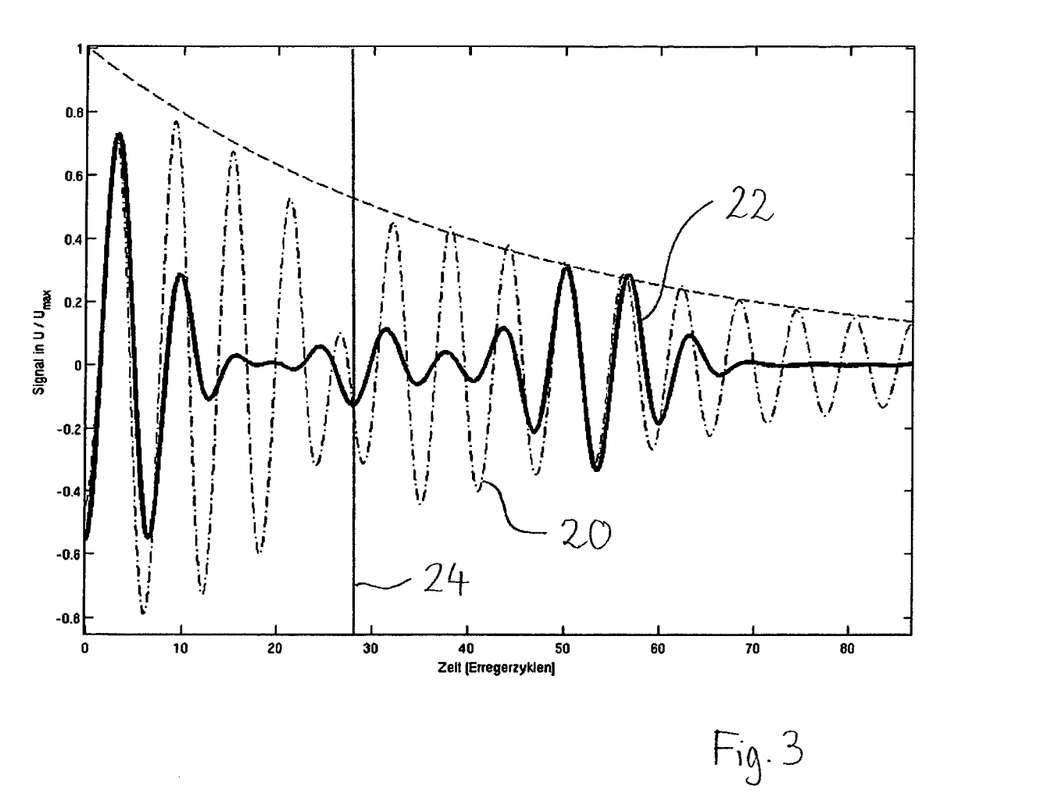
FIG. 3 shows the temporal profile of the superposed transverse magnetization of the exemplary cases according to FIG. 2 with echo generation.

FIG. 3 shows the profile of the superposed transverse magnetizations 20 or 22 according to FIG. 2, wherein, however, at the time 24, the rotation direction of the external rotating magnetic field is reversed. FIG. 3 thus shows the carrying out of an echo method. By reversing the rotation direction of the external rotating magnetic field, dephasing of the magnetization of small particles can be partially reversed. At a specific time point after the reversal of direction of rotation 24, a particular component of the magnetization of the small particles rotates in phase again. The observable measurement signal of the superposed transverse magnetization increases again.

In particular, the more quickly decaying transverse magnetization of the second particle ensemble can be evaluated much more precisely and with fewer measurement errors by using the echo method. The echo method provides temporally a wider measurement signal, which in the frequency space leads to a narrower bandwidth.

Figure 4:
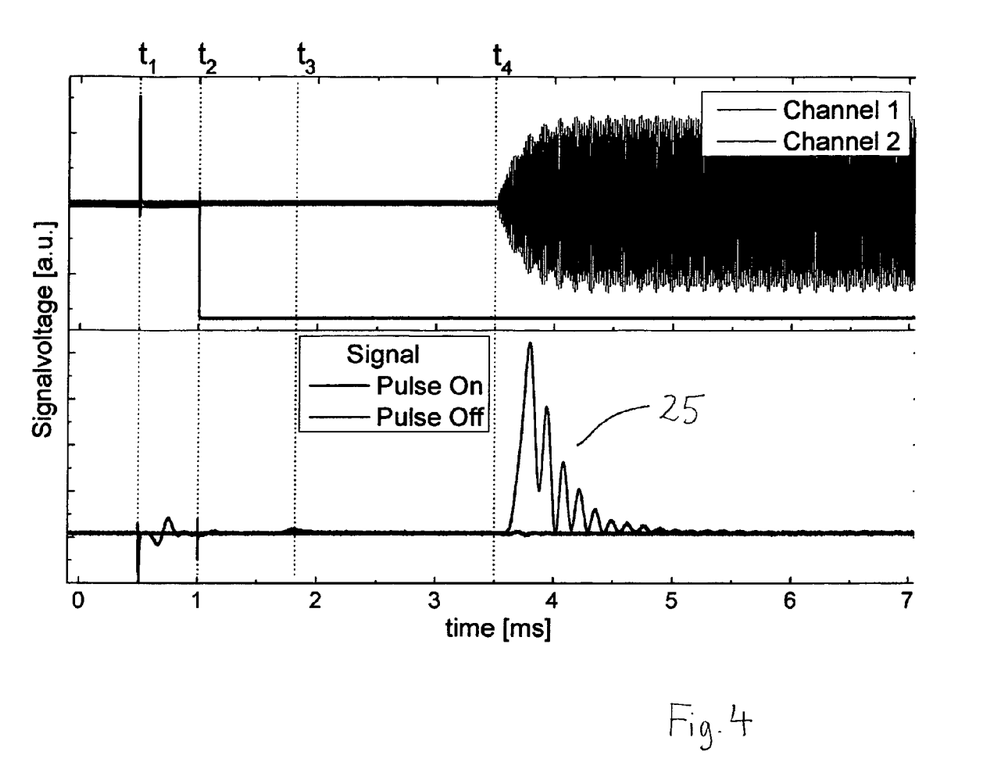
FIG. 4 shows the field profile of the preparing and measuring magnetic fields together with a measurement signal of the superposed transverse magnetization and FIG. 5 shows the profile of the superposed transverse magnetization for free and for bound small particles.

FIG. 4 shows, in the top half of the image, the profile of the magnetic fields for preparing and for reading a sample. The bottom half of the image shows the temporal profile of the observed superposed transverse magnetization 25. The echo method is carried out.

For the sake of comprehending FIG. 4, reference can be made to the apparatus 1 according to FIG. 1, which is suitable for carrying out the measurement method shown. As a sample, magnetic iron particles of a size of about 100 nm in water are investigated, which have a tendency to forming iron clusters with a size of about 100 μm.

At the time $t_1$, the Helmholtz coil pair 5a,b according to FIG. 1 is supplied with current in a pulsed manner. The result is a directed pulsed magnetic field with which the magnetizations of the iron particles are aligned. The directed magnetic field generated in a pulsed manner has approximately a full width at half maximum of 20 μs. A structure of the magnetic field pulse is not discernible in the figure.

Up to the time $t_2$, the induction coils 9a,b remain short-circuited. At time $t_2$, the induction coils 9a,b are activated. This measure ensures that no excitation signal can inductively pass into the measurement signal. The switch-off duration of the short-circuit of the induction coils causes a delay of their full reception readiness up to the time $t_3$.

At time $t_4$, that is to say after a delay time after the switching-off of the focusing field, the Helmholtz coil pairs 5a,b and 6a,b are in each case supplied with current of different frequencies. For example, one of the two coil pairs 5a,b is switched to a frequency of 50 kHz and the other coil pair 6a,b to a frequency of 58 kHz. With this specific provision of current, the result is a rotating external magnetic field in the measurement volume that periodically reverses its rotation direction. The frequency of the reversal of direction of rotation is here given by the beat frequency, that is to say (50 kHz−58 kHz)/2=4 kHz.

The result of the focusing field is a macroscopic magnetization by aligning the magnetic moments of the individual iron particles. The magnetization of the free iron particles relaxes within the set delay time. The macroscopic magnetization of the iron particles which are clustered together to form iron clusters persists on account of the slowed relaxation owing to the increasing size up to the switching-on of the rotating magnetic field. After the reading rotating external magnetic field is switched on, the magnetizations of the individual iron clusters begin to rotate asynchronously. To this end, the field strength of the rotating magnetic field is set accordingly.

Owing to the mechanical and magnetic coupling of the individual iron particles in the iron cluster, the superposed transverse magnetization quickly decays once the external rotating magnetic field is applied. The magnetic moments of the individual iron particles orient themselves increasingly randomly with respect to one another. The magnetizations of the iron clusters, which initially still rotate in phase, go out of phase. The echo signals of the profile of the superposed transverse magnetization 25 also decay quickly. The individual peaks/maxima in the profile of the transverse magnetization 25 reflect the echo frequency. The central asynchronous rotation frequency is not resolved in this illustration.

It becomes clear that with the method described, a clustering of the iron particles can be ascertained with impressive speed and reliability. A comparable signal results when the surfaces of the small magnetic particles are correspondingly prepared such that coupling to a specific partner, i.e. the analyte under investigation, or a clustering occurs therewith.

Figure 5:
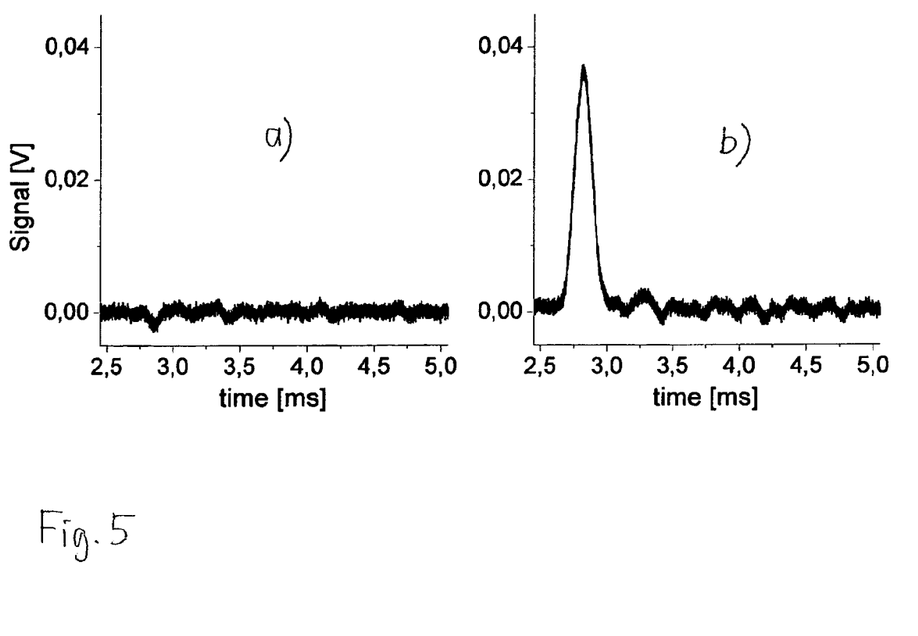

FIG. 5 shows the profile of the superposed transverse magnetization, as was measured according to FIG. 4, for two different sample preparations. The sample observed is of small magnetite particles with a diameter of 100 nm in water. The small magnetite particles have an anionic envelopment and are suitable in particular for adsorption of biomolecules. Such small particles are available for example from Chemiezell GmbH under the brand name fluidMAG. These are superparamagnetic nanoparticles.

In water, the anionic envelopment of the small particles results in no clustering taking place. To this extent, if the superposed transverse magnetization is measured as described previously in connection with FIG. 4, the macroscopic magnetization of said small particles, when the reading rotating external magnetic field is switched on, is already relaxed at approximately 2.5 ms. Accordingly, according to FIG. 5a no signal of the superposed transverse magnetization can be observed.

If cations are added to the water by adding a buffer solution, the anionic small particles couple via these cations from the solution to one another and form a particle cluster. The relaxation of the macroscopic magnetization of these clusters is impaired owing to the size increase or owing to a changed shape factor. When the reading rotating external magnetic field is applied, the result is a measurable superposed transverse magnetization. This can be seen clearly in FIG. 5. On the basis of the illustration and of measurement artifacts, no echo fluctuation of the measurement signal is discernible.

FIGS. 5a and 5b strikingly show that the previously described method is able to detect the presence of an analyte quickly and with great accuracy. With corresponding preparation, the small particles can be used as probes for detecting the specific analyte.

LIST OF REFERENCES

1 Apparatus
2 Measurement volume
3 Sample
5a,b First coil pair
6a,b Second coil pair
8 Measurement device
9a,b Induction coils
10 Control apparatus
11 Switch element
12 Low pass filter
20 Transverse magnetization (diffusion)
22 Transverse magnetization (inhomogeneities, particle scattering)
24 Field reversal
25 Echo signal
MFI, MFIII First magnetic field generator
MFII Second magnetic field generator
P1-P4 Coils
t1-t4 Times
x Transverse axis
y Transverse axis
z Longitudinal axis

The invention claimed is:

1. A method for drawing conclusions relating to presence of an analyte using an ensemble of small magnetic particles configured for interaction with the analyte, the method comprising
   (a) aligning the magnetizations of the small magnetic particles with one another using an external magnetic focusing field,
   (b) after step (a), switching off the external magnetic focusing field,
   (c) after step (b), using an external rotating magnetic field rotating about a longitudinal axis and having suitable field strength and rotation frequency to set the magnetizations of the small magnetic particles into a rotation which is asynchronous with the external rotating magnetic field,
   (d) detecting a temporal profile of a rotating superposed transverse magnetization of the ensemble of small magnetic particles, wherein the rotating superposed transverse magnetization rotates in a projection into a plane perpendicular to the longitudinal axis, and
   (e) drawing conclusions relating to the presence of the analyte from the temporal profile.

2. The method as claimed in claim 1, wherein the temporal profile is detected in step (d) after a specified delay time after the external magnetic focusing field has been switched off in step (b).

3. The method as claimed in claim 1, wherein the temporal profile is detected in step (d) only after a dead time after the external magnetic focusing field has been switched off in step (b).

4. The method as claimed in claim 1, wherein step (e) comprises:
   (e1) forming a time derivation from the temporal profile, and
   (e2) drawing the conclusions relating to the presence of the analyte from the time derivation.

5. The method as claimed in claim 1, wherein step (c) further comprises reversing the direction of rotation of the external rotating magnetic field with an echo frequency.

6. The method as claimed in claim 1, wherein the external rotating magnetic field is generated in step (c) using two coil pairs or coil arrangements, which are perpendicular to each other wherein the two coil pairs are driven using time-varying phase differences.

7. The method as claimed in claim 1, wherein the external magnetic focusing field is produced in step (a) as an external rotating magnetic field having a field strength greater than a field strength of the external rotating magnetic field of step (c).

8. The method as claimed in claim 7, wherein step (a) further comprises generating a refocusing field such that the magnetizations of small magnetic particles of identical rotation characteristics are selectively set into a synchronous rotation.

9. The method as claimed in claim 1, wherein step (e) further comprises, on the basis of the temporal profile, drawing conclusions relating to concentration of the analyte.

10. The method as claimed in claim 1, wherein step (a) further comprises adding functional groups, which bind to the analyte, to the small magnetic particles.

11. The method as claimed in claim 1, wherein step (e) further comprises detecting physical and/or chemical environmental parameters of the analyte.

12. The method as claimed in claim 1, wherein, for phase encoding, step (c) further comprises producing a first magnetic gradient field for a predetermined time interval.

13. The method as claimed in claim 12, wherein step (c) further comprises:
   switching off the first magnetic gradient field after a first instance of the predetermined time interval, and
   producing a second identical magnetic gradient field with the opposite sign for a second instance of the predetermined time interval, and wherein the temporal profile is detected in step (d) after the second instance of the predetermined time interval.

\* \* \* \* \*